(12) United States Patent
Malka

(10) Patent No.: US 8,568,658 B1
(45) Date of Patent: Oct. 29, 2013

(54) INFANT PACIFIER STERILIZATION ASSEMBLY

(71) Applicant: Moti Malka, Encino, CA (US)

(72) Inventor: Moti Malka, Encino, CA (US)

(*) Notice: Subject to any disclaimer, the term of this patent is extended or adjusted under 35 U.S.C. 154(b) by 0 days.

(21) Appl. No.: 13/653,558

(22) Filed: Oct. 17, 2012

(51) Int. Cl.
*A61L 2/18* (2006.01)

(52) U.S. Cl.
USPC .............................. 422/28; 422/292; 422/300

(58) Field of Classification Search
USPC .......................................... 422/28, 292, 300
See application file for complete search history.

(56) References Cited

U.S. PATENT DOCUMENTS

| 5,402,810 | A | 4/1995 | Donley |
| D358,243 | S | 5/1995 | Ferguson |
| 5,722,537 | A | 3/1998 | Sigler |
| 6,343,612 | B1 | 2/2002 | Dahl |
| 7,207,342 | B1 | 4/2007 | Daniels |
| 2007/0012248 | A1 | 1/2007 | Aucoin |
| 2008/0289975 | A1* | 11/2008 | Sharber .................. 206/207 |

FOREIGN PATENT DOCUMENTS

JP 10-035705 * 2/1998 ............. B65D 45/34

OTHER PUBLICATIONS

English machine translation of JP 10-035705 Matsuyama et al. Feb. 1998. Retrieved from Industrial Property Digital Library.*
"Non-Toxic Homemade Bubbles and 5 More Fun Backyard Activities" Emily. Jul. 2011. Retrieved from simplehomemade.net.*

* cited by examiner

*Primary Examiner* — Sean E Conley
*Assistant Examiner* — Donald Spamer

(57) ABSTRACT

An infant pacifier sterilization assembly includes a housing that has an aperture extending through a top of the housing. An antiseptic compound is contained within the housing. The antiseptic compound is nontoxic. A valve is positioned within the aperture. The valve insertably receives a nipple on a pacifier so the nipple is submerged in the antiseptic compound. The valve is a one-way valve so the antiseptic compound is retained in the housing.

7 Claims, 4 Drawing Sheets

INFANT PACIFIER STERILIZATION ASSEMBLY

BACKGROUND OF THE DISCLOSURE

Field of the Disclosure

The disclosure relates to infant pacifier sterilization devices and more particularly pertains to a new infant pacifier sterilization device for sterilizing a nipple on the pacifier.

SUMMARY OF THE DISCLOSURE

An embodiment of the disclosure meets the needs presented above by generally comprising a housing that has an aperture extending through a top of the housing. An antiseptic compound is contained within the housing. The antiseptic compound is nontoxic. A valve is positioned within the aperture. The valve insertably receives a nipple on a pacifier so the nipple is submerged in the antiseptic compound. The valve is a one-way valve so the antiseptic compound is retained in the housing.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
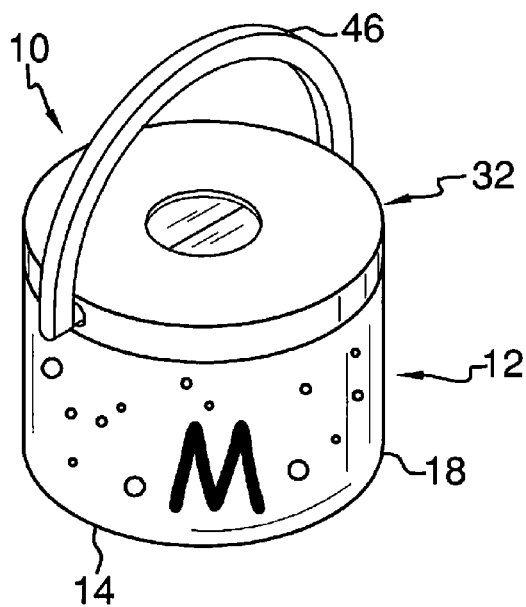
FIG. 1 is a perspective view of a infant pacifier sterilization assembly according to an embodiment of the disclosure.
Figure 2:
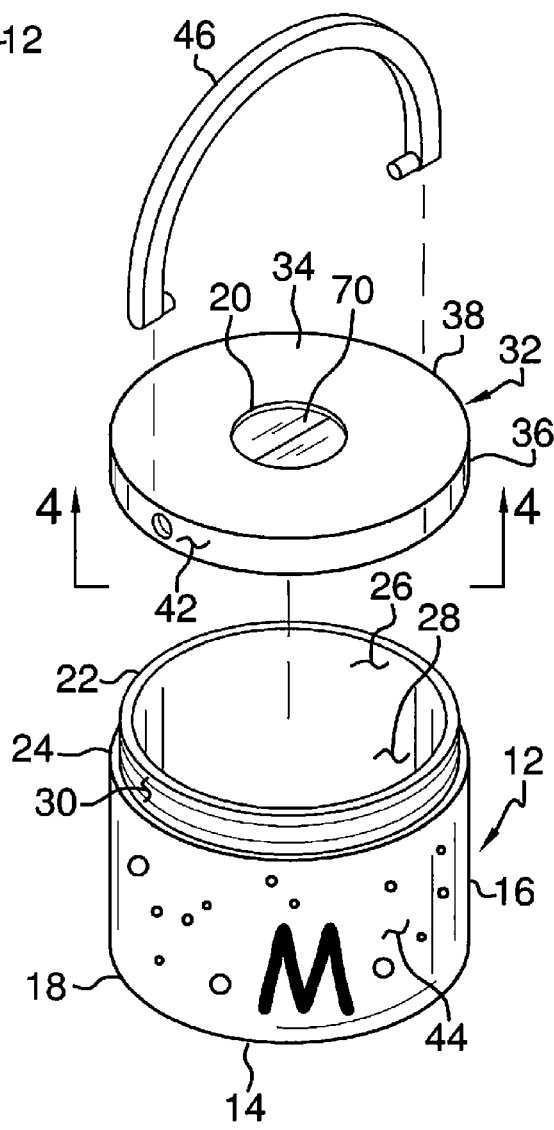
FIG. 2 is a top perspective view of an embodiment of the disclosure.
Figure 3:
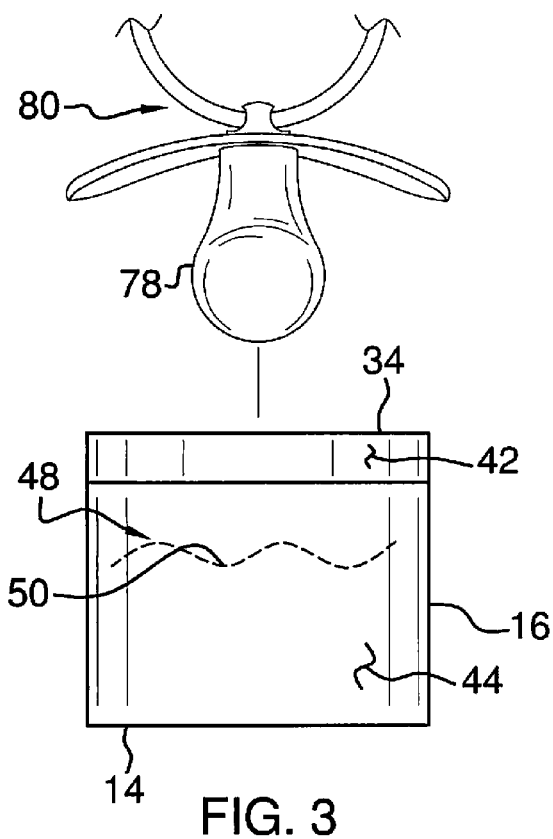
FIG. 3 is a front view of an embodiment of the disclosure.
Figure 4:
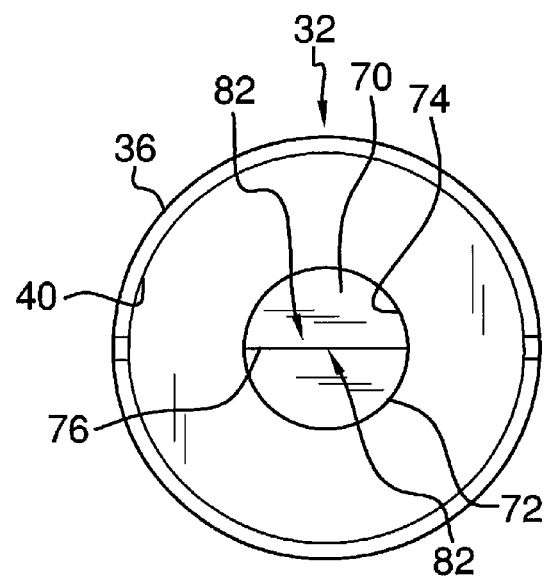
FIG. 4 is a top view of an embodiment of the disclosure.
Figure 5:
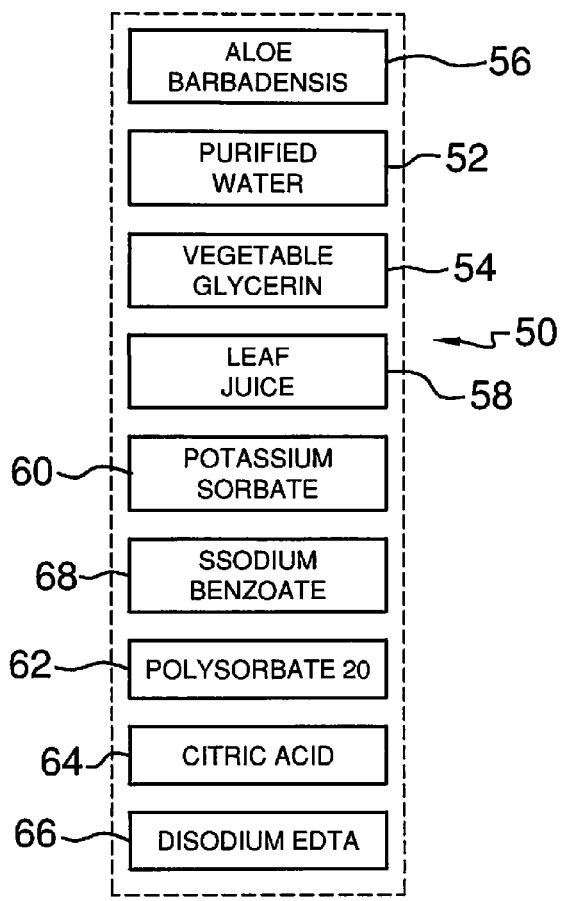
FIG. 5 is a chemical schematic view of an embodiment of the disclosure.
Figure 6:
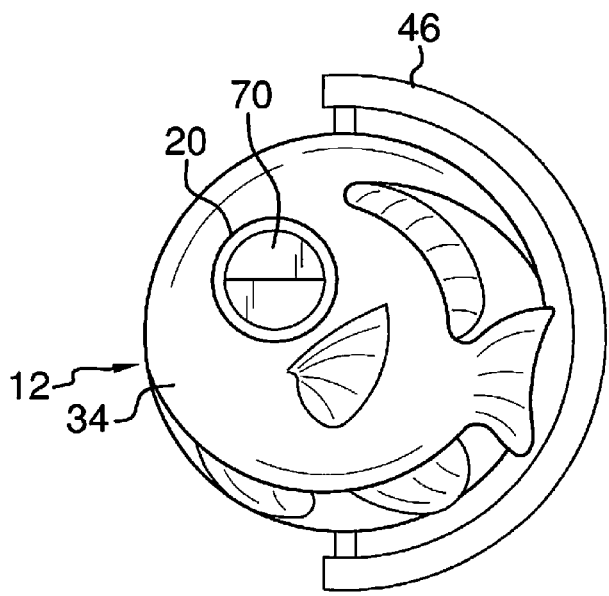
FIG. 6 is a top view of an alternative embodiment of the disclosure.
Figure 7:
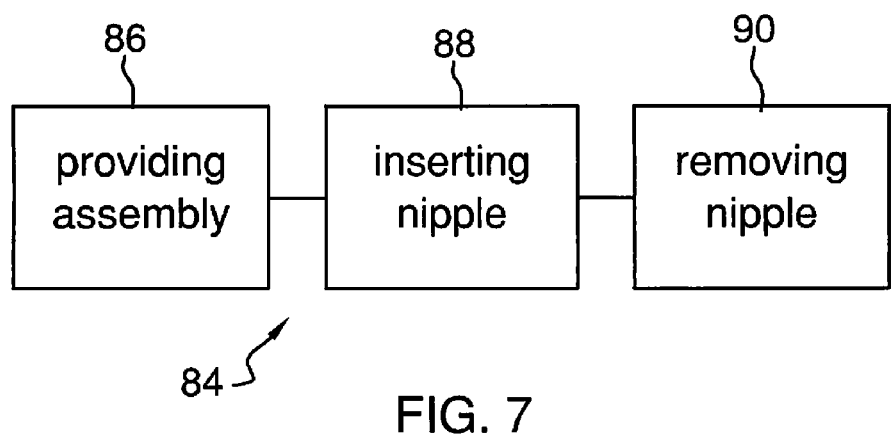
FIG. 7 is a schematic view of an embodiment of the disclosure.

With reference now to the drawings, and in particular to FIGS. 1 through 7 thereof, a new infant pacifier sterilization device embodying the principles and concepts of an embodiment of the disclosure and generally designated by the reference numeral 10 will be described.

As best illustrated in FIGS. 1 through 7, the infant pacifier sterilization assembly 10 generally comprises a housing 12 including a bottom wall 14 and a perimeter wall 16 coupled to and extending upwardly from an exterior edge 18 of the bottom wall 14. The perimeter wall 16 includes a coupler portion 22 extending upwardly from a top edge 24 of the perimeter wall 16 so an inner surface 26 of the coupler portion 22 is coextensive with an inside surface 28 of the perimeter wall 16. An outer surface 30 of the coupler portion 22 is threaded. The housing 12 may have a cylindrical shape. The housing 12 may alternatively have a decorative shape of an animal, such as a fish, or a turtle, or other animal.

A lid 32 is positionable on the housing 12. The lid 32 includes a top wall 34 and a peripheral wall 36 coupled to and extending downwardly from an external edge 38 of the top wall 34. An interior surface 40 of the peripheral wall 36 threadably engages the coupler portion 22 of the housing 12 so an extraneous surface 42 of the peripheral wall 36 is coextensive with an outside surface 44 of the perimeter wall 16 of the housing 12. The top wall 34 of the lid 32 has an aperture 20 extending therethrough. The lid 32 may have a shape to match the shape of the housing 12. A handle 46 is movably coupled to the peripheral wall 36 of the lid 32. The handle 46 may provide a grip to carry the housing 12.

An antiseptic compound 48 is contained within the housing 12. The antiseptic compound 48 is a liquid 50. The liquid 50 is a mixture of purified water 52, vegetable glycerin 54, aloe barbadensis 56, waterleaf juice 58, potassium sorbate 60, polysorbate 20 62, citric acid 64, disodium edta 66 and sodium benzoate 68. The liquid 50 may have a concentration of waterleaf juice 58 between 10 percent and 15 percent of total volume and a concentration of aloe barbadensis 56 between 5 percent and 10 percent total volume. The liquid 50 may have a concentration of purified water 52 between 70 percent and 80 percent of total volume.

A valve 70 is positioned within the aperture 20 such that a peripheral edge 72 of the valve 70 is coupled to an inner edge 74 of the aperture 20 so the valve 70 covers the aperture 20. The valve 70 has a cut 76 extending laterally across the valve 70. The cut 76 insertably receives a nipple 78 on a pacifier 80 so the nipple 78 is submerged in the antiseptic compound 48. The cut 76 closes after the nipple 78 is removed so the antiseptic compound 48 is retained in the housing 12. The valve 70 may be comprised of a resiliently deformable material such as rubber or other similar material. The sides 82 of the cut 76 may abut so the antiseptic compound 48 may not exit through the cut 76. The sides 82 of the cut 76 may be parted by the nipple 78 in order to submerge the nipple 78 in the antiseptic compound 48.

In use, a method 84 of sterilizing the nipple 78 on the pacifier 80 comprises the steps 86 of providing a housing 12 and an antiseptic compound 78. The antiseptic compound 48 is contained within the housing 12. The housing 12 includes a lid 32. The lid 32 has an aperture 20 extending therethrough. The lid 32 includes a valve 70 positioned within the aperture 20. The method 84 includes the step 88 of inserting the nipple 78 on the pacifier 80 through the valve 70 so the nipple 78 is submerged in the antiseptic compound 78. The method 84 finally includes the step 90 of removing the nipple 78 from the valve 70 so the valve 70 closes to retain the antiseptic compound 48 within the housing 12.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure.

I claim:

1. An infant pacifier sterilization assembly configured to have the pacifier submerged in an antiseptic compound, said assembly comprising:
   a housing having an aperture extending through a top of said housing;
   an antiseptic compound contained within said housing, said antiseptic compound being nontoxic, said antiseptic compound being a liquid, said liquid being a mixture of purified water, vegetable glycerin, aloe barbadensis, waterleaf juice, potassium sorbate, polysorbate 20, citric acid, disodium EDTA and sodium benzoate; and
   a valve positioned within said aperture, said valve insertably receiving a nipple on a pacifier such that said nipple is submerged in said antiseptic compound, said valve being a one-way valve whereby said antiseptic compound is retained in said housing.

2. The assembly according to claim 1, further including said housing including a bottom wall and a perimeter wall coupled to and extending upwardly from an exterior edge of said bottom wall, said perimeter wall including a coupler portion extending upwardly from a top edge of said perimeter wall whereby an inner surface of said coupler portion is coextensive with an inside surface of said perimeter wall, an outer surface of said coupler portion being threaded.

3. The assembly according to claim 2, further including a lid being positionable on said housing, said lid including a top wall and a peripheral wall coupled to and extending downwardly from an external edge of said top wall, an interior surface of said peripheral wall threadably engaging said coupler portion of said housing whereby an extraneous surface of said peripheral wall is coextensive with an outside surface of said perimeter wall of said housing, said top wall of said lid having an aperture extending therethrough.

4. The assembly according to claim 1, further including a lid being positionable on said housing, said lid including a top wall, said top wall of said lid having an aperture extending therethrough, said valve being positioned within said aperture such that a peripheral edge of said valve is coupled to an inner edge of said aperture whereby said valve covers said aperture, said valve having a cut extending laterally across said valve, said cut insertably receiving a nipple on a pacifier whereby the nipple is submerged in said antiseptic compound, said cut closing after the nipple is removed whereby said antiseptic compound is retained in said housing.

5. The assembly according to claim 3, further including a handle movably coupled to said peripheral wall of said lid, said handle being configured to provide a grip to carry said housing.

6. An infant pacifier sterilization assembly configured to have the pacifier submerged in an antiseptic compound, said assembly comprising:
   a housing including a bottom wall and a perimeter wall coupled to and extending upwardly from an exterior edge of said bottom wall, said perimeter wall including a coupler portion extending upwardly from a top edge of said perimeter wall whereby an inner surface of said coupler portion is coextensive with an inside surface of said perimeter wall, an outer surface of said coupler portion being threaded;
   a lid being positionable on said housing, said lid including a top wall and a peripheral wall coupled to and extending downwardly from an external edge of said top wall, an interior surface of said peripheral wall threadably engaging said coupler portion of said housing whereby an extraneous surface of said peripheral wall is coextensive with an outside surface of said perimeter wall of said housing, said top wall of said lid having an aperture extending therethrough;
   an antiseptic compound contained within said housing, said antiseptic compound being a liquid, said liquid being a mixture of purified water, vegetable glycerin, aloe barbadensis, waterleaf juice, potassium sorbate, polysorbate 20, citric acid, disodium EDTA and sodium benzoate;
   a valve being positioned within said aperture such that a peripheral edge of said valve is coupled to an inner edge of said aperture whereby said valve covers said aperture, said valve having a cut extending laterally across said valve, said cut insertably receiving a nipple on the pacifier whereby the nipple is submerged in said antiseptic compound, said cut closing after the nipple is removed whereby said antiseptic compound is retained in said housing; and
   a handle movably coupled to said peripheral wall of said lid, said handle being configured to provide a grip to carry said housing.

7. A method of sterilizing a nipple on a pacifier, the steps of the method comprising:
   providing a housing having an aperture extending through a top of said housing, and providing an antiseptic compound, said antiseptic compound being nontoxic and contained within said housing, said antiseptic compound being a liquid, said liquid being a mixture of purified water, vegetable glycerin, aloe barbadensis, waterleaf juice, potassium sorbate, polysorbate 20, citric acid, disodium EDTA and sodium benzoate, and providing a valve positioned within said aperture, said valve being a one-way valve whereby said antiseptic compound is retained in said housing;
   inserting the nipple on the pacifier through said valve whereby the nipple is submerged in said antiseptic compound; and
   removing the nipple from said valve whereby said valve closes to retain said antiseptic compound within said housing.

* * * * *